United States Patent [19]
Smith et al.

[11] 4,112,014
[45] Sep. 5, 1978

[54] O,O'-BIS(HYDROXYALKYL) N,N-DI(LOWER-ALKYL)AMINOMETHANE PHOSPHONATES

[75] Inventors: Curtis P. Smith, Cheshire; Henri Ulrich, Northford, both of Conn.

[73] Assignee: The Upjohn Company, Kalamazoo, Mich.

[21] Appl. No.: 786,690

[22] Filed: Apr. 11, 1977

Related U.S. Application Data

[63] Continuation of Ser. No. 634,136, Nov. 21, 1975, abandoned.

[51] Int. Cl.$^2$ ............................. C07F 9/40; C08J 9/00
[52] U.S. Cl. ................................... 260/945; 252/182; 260/976; 521/165
[58] Field of Search ......................................... 260/945

[56] References Cited

U.S. PATENT DOCUMENTS

| 3,314,957 | 4/1967 | Friedman | 260/945 X |
| 3,707,587 | 12/1972 | Schliebs et al. | 260/945 X |

Primary Examiner—Anton H. Sutto
Attorney, Agent, or Firm—Denis A. Firth; John Kekich

[57] ABSTRACT

Bis(2-hydroxyalkyl) N,N-di(lower-alkyl)aminomethylphosphonates are described. These phosphorus-containing polyols can be incorporated into polyurethane foams to render the latter fire retardant. They have the advantage over closely related phosphorus-containing polyols that they are autocatalytic in the polyurethane foam forming reaction and that they can be mixed with the polyol component of the polyurethane foam forming composition to give a mixture (premix) which can be maintained in storage for prolonged periods without showing any signs of deterioration.

4 Claims, No Drawings

O,O'-BIS(HYDROXYALKYL) N,N-DI(LOWER-ALKYL)AMINOMETHANE PHOSPHONATES

This is a continuation of application Ser. No. 634,136 filed Nov. 21, 1975, now abandoned.

BACKGROUND OF THE INVENTION

1. Field of the Invention

This invention relates to novel polyols and to processes for their preparation and is more particularly concerned with novel phosphorus-containing polyols and with processes for their preparation and with their use in the preparation of fire retardant foams.

2. Background of the Invention

A prodigious amount of research has been devoted in recent years to the development of phosphorus-containing compounds which possess active hydrogen containing groups such as hydroxyl and amino and which can, therefore, be incorporated chemically into polyurethane and like polymers. The incorporation of such phosphorus containing compounds into polymers generally results in some degree of enhancement of the flame retardant properties of the polymer. However many of the phosphorus containing compounds so investigated have proved to be of no practical importance because of undesirable side effects such as an adverse change in physical properties of the resulting polymer, incompatibility with the other components of the polymer forming mixture, and the like.

One of the more successful groups of phosphorus compounds of the above type, which has been developed and widely used in imparting fire retardance to polyurethane foams, is that represented by the formula:

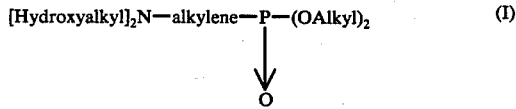

Within this group the compound diethyl N,N-di(2-hydroxyethyl)aminomethylphosphonate is widely known and used commercially; see U.S. Pat. No. 3,076,010.

Unfortunately, this compound and the class to which it belongs share a disadvantage which is common to many other potentially useful phosphorus containing polyols in that they are unstable when stored for extended periods of time in combination with other components normally employed in the fabrication of polyurethanes. It is common practice to supply two component systems for the manufacture of polyurethanes, one component being a polyisocyanate or an isocyanate-terminated prepolymer, and the second component being a mixture of polyols, surfactants, catalysts, and the like additives. The two components are stored separately until it is desired to produce the desired polyurethane at which point the two components are mixed and allowed to react.

When a phosphorous containing polyol, such as the particular ones discussed above, is to be employed in a two component system for the production of polyurethanes, it is desirable to include it as part of the component which contains the polyol and other ingredients. Obviously, the phosphorus-containing polyol cannot be incorporated in the polyisocyanate component because of the interaction which would take place. It is, therefore, desirable that any phosphorus polyol which is to be employed in the above manner be stable when stored in admixture with the polyol and other ingredients of the polyol component. It is an object of the invention to provide a phosphorus-containing polyol which meets this criterion and which is also capable of imparting fire retardant properties to polyurethanes without exerting any deleterious effects on the physical properties of the latter. Other objects of the invention will become apparent as the description of the invention proceeds.

Many compounds closely related chemically to the known compounds of formula (I) above have been described in the art. Illustratively, U.S. Pat. No. 3,314,957 shows bis(dialkylene glycol) dialkylaminomethanephosphonates and related compounds and their use in the synthesis of polyurethanes. Substantially the same group of compounds is also disclosed in U.S. Pat. No. 3,549,728. U.S. Pat. Nos. 3,457,333 and 3,539,536 both show the corresponding bis(hydroxypolyalkoxyalkyl) N,N-di(hydroxyalkyl)aminomethanephosphonates and their use in the synthesis of fire retardant polyurethanes. U.S. Pat. Nos. 3,480,594 and 3,480,699 show O-(hydroxyalkoxy)-O'-hydroxyalkyl N,N-di(hydroxyalkyl)aminomethanephosphonates and fire retardant polyurethanes derived therefrom. U.S. Pat. No. 3,567,801 shows generically, but not specifically, di(hydroxyalkoxy) aminomethanephosphonates in which the two nitrogen atoms can be unsubstituted. U.S. Pat. No. 3,707,587 is concerned with a process for preparing, inter alia, di(hydroxyalkyl) N,N-di(hydroxyalkyl)aminomethanephosphonates by reacting dialkanolamines with spirocyclic phosphorus compounds obtained, for example, by reacting alkylene-1,2-glycols with trialkylphosphites.

We have now found that a certain narrow class of esters of N,N-disubstituted aminomethanephosphoric acid possess properties which are highly advantageous and which distinguish them from the many such esters of this class hitherto known.

SUMMARY OF THE INVENTION

This invention comprises O,O'-bis(2-hydroxyalkyl) N,N-di(lower-alkyl)aminomethanephosphonates having the formula:

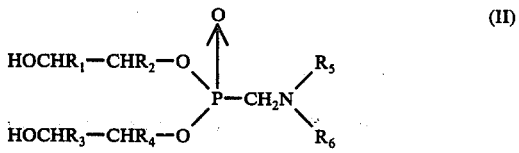

wherein $R_1$, $R_2$, $R_3$ and $R_4$ are each independently selected from the group consisting of hydrogen and lower-alkyl, and $R_5$ and $R_6$ each independently represents lower-alkyl.

The invention also comprises storage stable polyol component premixes which contain the above compounds (II) and which are adapted for use in multi-component systems for the preparation of polyurethanes.

The invention also comprises flame retardant polyurethanes derived from the compounds (II) and more particularly those in which the compounds (II) serve as part of the polyol component and also serve as catalysts in the polyurethane forming reaction.

The term "lower-alkyl" is used herein in its conventionally accepted sense as meaning alkyl having from 1 to 6 carbon atoms, inclusive, such as methyl, ethyl, propyl, butyl, pentyl, hexyl and isomeric forms thereof.

DETAILED DESCRIPTION OF THE INVENTION

The compounds of the formula (I) are obtained conveniently by reaction of the corresponding spirocyclic phosphorus compounds of the formula:

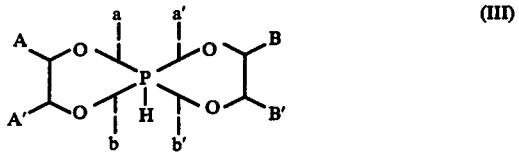
(III)

wherein A, A', B and B' are independently selected from the group consisting of hydrogen and lower-alkyl, with formaldehyde and the appropriate di(lower-alkyl)amine $R_5R_6NH$ under Mannich reaction conditions. The above formula (III) represents only one of a number of possible isomers which can occur when A, A', B, B' or any of them are other than hydrogen, because of the stereoisomerism about the phosphorus atom. The formula (III) has been used for the sake of simplicity to represent all the possible isomers which are obtained in the preparation of this compound by the methods which will be described hereinafter.

The above reaction is represented schematically as follows:

It will be seen that the reaction leads to ring opening of the spirocyclic phosphorus compound (III) to form the hydroxyalkyl ester groups which are represented in the formula for compound (II) as HO—$CHR_1$—$CHR_2$— and HO—$CHR_3$—$CHR_4$— wherein $R_1$, $R_2$, $R_3$ and $R_4$ are as hereinbefore defined. It will also be seen that each of the two rings in the spirocyclic phosphoric compound (III) can open in either of two ways, i.e. either at linkage (a) or linkage (b) in the case of the one ring and at linkage (a') or (b') in the case of the other ring. Illustratively, ring opening at linkage (a) will give rise to the group

whereas opening of the same ring at linkage (b) will give rise to the group

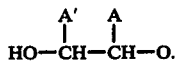

Similar ring opening of the other ring in compound (III) at linkage a' will give rise to the group spirocyclic compound quantitative

and ring opening at linkage b' will give rise to the group

It is believed that the product obtained in the above reaction is a mixture of products some of which are derived by ring opening at linkages a and a', some by ring opening at linkages b and b' and some by ring opening at combinations of a and b' or b and a'. Accordingly, the product obtained in any instance has been designated by formula (II) and it is to be understood that this formula, except in the case wherein each of $R_1$, $R_2$, $R_3$ and $R_4$ represent hydrogen, encompasses a mixture of the various possible products derived by ring opening of the spirocyclic compound (III) in the various ways discussed above. Analytical techniques presently available do not permit of a quantitative analysis of the proportions of the various possible isomeric forms of the hydroxyalkyl groups in the compound (II).

The reaction between the spirocyclic phosphorus compound (III), the formaldehyde and the secondary amine $HNR_5R_6$ is carried out readily by bringing the reactants together in substantially equimolar proportions. The reaction conditions employed are those of the well-known Mannich reaction; see, for example. Organic Reactions, Adams, Vol. 1, pp. 303–330, Wiley, New York, New York, 1942. Preferably the spirocyclic phosphorus compound (III) and the formaldehyde are brought together first in any convenient manner and the secondary amine is added to the resulting mixture. The reaction is generally exothermic although it is generally necessary to provide heat initially to promote the reaction. Thus the initial mixture of the compound (III) and formaldehyde can be heated to about 60° C or higher before addition of the secondary amine begins and thereafter the temperature of the reaction mixture is advantageously maintained in the range of about 50° to about 80° C until reaction is complete. The latter occurrence can be determined readily by routine analytical procedures, for example, by observing the disappearance of the absorption band corresponding to the P—H bond in the infrared absorption spectra of an aliquot of the reaction mixture.

If desired the above reaction can be carried out in the presence of an inert organic solvent such as methylene chloride, benzene, chlorobenzene, toluene, xylene, carbon tetrachloride and the like. However, the use of such solvents is generally unnecessary unless it is otherwise difficult to control the exotherm generated in the reaction.

The desired product (II) is isolated from the reaction product obtained as described above by removing the more volatile products by distillation advantageously under reduced pressure. The product so obtained generally contains traces of acid material. It is believed that the latter arises during the reaction by the formation of small amounts of compounds having free hydroxyl groups attached to phosphorus, which compounds arise during ring opening of the spirocyclic phosphorus compound (III). Irrespective of the cause of formation of the acidity, it is desirable to eliminate said acidity in the product. This can be done by any of the conventional methods known in the art for eliminating acidity in polyols. Advantageously, the acidity is corrected by reacting the crude product (II), obtained as described above, with a minor amount of an alkylene oxide, preferably propylene oxide.

The proportion of alkylene oxide required will vary from batch to batch of the product (II) since the amount of acidity will vary. The proportion of alkylene oxide required in any given instance can readily be determined by trial and error. It is important to note that the reaction of the compound (II) with the alkylene oxide under the conditions employed does not involve any significant reaction of the alkylene oxide with the hydroxyl groups of the hydroxyalkyl radicals in said compounds.

After the above described treatment, the compound (II) obtained as described above is then ready for use in the preparation of polyurethanes, and of polyol component premixes therefor, as will be described in more detail hereinafter.

The spirocyclic phosphorus compounds (III) are, in many cases, known compounds and all can be prepared by methods known in the art; see, for example, U.S. Pat. No. 3,707,587. We have found that, in addition to the method described in the latter reference, which method involves the reaction of propyleneglycol-1,2 or any corresponding vicinal alkanediol with trimethylphosphite, the compound (III) can be prepared by a novel and relatively inexpensive procedure which will now be described. This process can be represented schematically as follows:

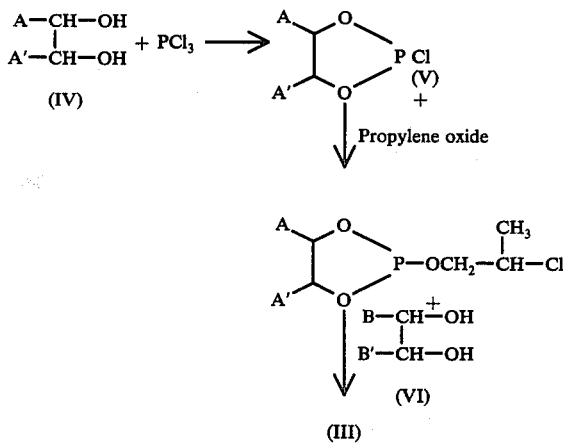

A, A', B and B' have the significance hereinbefore defined.

The various steps shown above can be carried out in a single continuous manner without the need to isolate the various intermediates. In the initial step the alkylene glycol (IV) is added slowly, with agitation and under an atmosphere of inert gas such as nitrogen, to the phosphorus trichloride. The reactants are employed in approximately equimolar proportions. The temperature of the reaction mixture is maintained advantageously in the range of about 0° to 25° C and preferably in the range of 5° to 10° C during the addition and thereafter until the desired reaction is found to be complete as determined by routine analytical procedures such as infrared spectroscopy. The resulting product (V) is then maintained in the same range of temperature described above while an approximately equimolar proportion of propylene oxide is added.

When the addition is complete, i.e. the second step shown above is complete, the final step of the process is accomplished by addition, with agitation, of an approximately equimolar proportion of the second alkylene glycol (VI). This second alkylene glycol can be the same as the initial glycol (IV) or can be different. The temperature during this final addition is again maintained in the same range as that employed in the previous steps. The resulting reaction mixture is maintained in said temperature range until the reaction is adjudged to be complete as determined by routine analytical procedures such as infrared spectroscopy. The desired product (III) is isolated from the reaction product by stripping of volatile materials by distillation, advantageously under reduced pressure. The product (III) can be purified, if desired, by conventional procedures such as chromatography, distillation and the like.

The phosphorus containing polyols (II) of the invention can be employed in the preparation of polyurethanes and thereby impart fire retardance thereto. The methods conventionally employed in the art for the preparation of polyurethanes can be employed in preparing fire retardant polyurethanes in accordance with this invention. The novel feature is replacement of part of the polyol conventionally employed by an equivalent amount of a phosphorus containing polyol (II) or a mixture of two or more such polyols. The amount of the polyol (II) which is employed in this manner is advantageously sufficient to impart to the resulting polyurethane a content of phosphorus in the range of about 0.5 to about 3 percent. This content of phosphorus in the final product is achieved by employing from about 0.05 to about 0.3 equivalents of the phosphorus containing polyol (II), or a mixture of two or more such polyols, per equivalent of the polyisocyanate employed in the reaction mixture.

While the use of the phosphorus-containing polyols (II) can be applied to the formation of any type of polyurethane, including cellular and non-cellular polyurethanes, it is of particular application to the preparation of cellular polyurethanes both flexible and rigid as well as those foams which are intermediate between the two and are commonly referred to as semi-flexible or semi-rigid. A comprehensive account of the techniques conventionally employed in the art for the preparation of cellular and non-cellular polyurethanes by the interaction of polyisocyanates and polyols, is to be found in Saunders and Frisch, Polyurethanes, Chemistry and Technology, Part II, 1964, Interscience Publishers, New York. These techniques are so well-known and familiar to one skilled in the art that it is unnecessary to give a detailed account thereof.

Thus, any of the polyisocyanates and polyols conventionally employed in the art can be used in preparing polyurethanes in accordance with this invention provided that a portion of the polyol component, within the limits discussed above, is replaced by the phosphorus containing polyol of formula (II). Illustrative of the organic polyisocyanates are 2,4-toluene diisocyanate, 2,6-toluene diisocyanate, 4,4'-methylenebis(phenyl isocyanate), 2,4'-methylenebis(phenyl isocyanate), dianisidine diisocyanate, tolidine diisocyanate, hexamethylene diisocyanate, m-xylylene diisocyanate, 1,5-naphthalene diisocyanate, p-phenylene diisocyanate, 1,4-diethylbenzene-$\beta,\beta'$-diisocyanate, tri(4isocyanatophenyl)methane, and other di- and higher polyisocyanates such as those listed in the tables of Siefken, Annalen, 562, 122-135, 1949. Mixtures of two or more of the above isocyanates can be used, such as mixtures of the 2,4- and 2,6- isomers of toluene diisocyanate, mixtures of 2,4'- and 4,4'-methylenebis(phenyl isocyanate) and the like.

In addition to the various isomers of methylenebis(phenyl isocyanate) and mixtures of these isomers, there can also be used modified forms of these isocyanates. For example, there can be used 4,4'-methylenebis(phenyl isocyanate), or an admixture thereof with a minor amount of the 2,4'-isomer, which has been treated to convert a minor proportion, generally less than 15 percent by weight of the starting material, to an artefact of the latter. For example, the polyisocyanates employed in making the polyurethane foams of the invention can be methylenebis(phenyl isocyanate) which has been converted to a stable liquid form in accordance with the process of U.S. Pat. No. 3,384,653. Illustrative of another form of modified methylenebis(phenyl isocyanate) is the product obtained by treating 4,4'-methylenebis(phenyl isocyanate), or mixtures thereof with the 2,4'-isomer, with a minor proportion of a carbodiimide such as diphenylcarbodiimide in accordance with the process described in British Pat. No. 918,454.

In addition to the di- and higher polyisocyanates illustrated above, the organic polyisocyanates employed in the preparation of the polyurethane foams of the invention include the isocyanate-terminated prepolymers obtained by reacting an excess of any of the polyisocyanates discussed above with a polyol. The polyols employed in making the isocyanate-terminated prepolymers can be any of those conventionally employed in the art for this purpose. Advantageously, said polyols have an hydroxy equivalent weight of about 30 to about 2,000 and a functionality from 2 to 4. Preferably, said polyols are diols, i.e. have a functionality of 2.

The polyols employed in making polyurethane foams in accordance with the process of the invention can be polyester or polyether polyols, advantageously those having a functionality from 2 to 6 and an equivalent weight from 90 to about 2000. Illustrative of the polyether polyols are polyoxyalkylene glycols such as polytetramethylene glycol, the polyoxyethylene glycols prepared by the addition of ethylene oxide to water, ethylene glycol or diethylene glycol; polyoxypropylene glycols prepared by the addition of 1,2-propylene oxide to water, propylene glycol or dipropylene glycol; mixed oxyethylene oxypropylene glycols prepared in a similar manner utilizing a mixture of ethylene oxide or propylene oxide or a sequential addition of ethylene oxide and 1,2-propylene oxide; polyether glycols prepared by reacting ethylene oxide, propylene oxide, or mixtures thereof with mono- and polynuclear dihydroxybenzene, e.g. catechol, resorcinol, hydroquinone, orcinol, 2,2-bis(p-hydroxyphenyl)propane, bis(p-hydroxyphenyl)methane and the like; and polyethers prepared by reacting ethylene oxide, propylene oxide, or mixtures thereof with aliphatic polyols such as glycerol, trimethylolpropane, 1,2,6-hexanetriol, and the like.

Illustrative of polyester polyols are those prepared by polymerizing ε-caprolactone using an initiator such as ethylene glycol, ethanolamine and the like, and those prepared by esterification of polycarboxylic acids such as phthalic, terephthalic, succinic, glutaric, and adipic acids and the like, with polyhydric alcohols such as ethylene glycol, butanediol, glycerol, trimethylolpropane, 1,2,6-hexanetriol and the like.

As set forth above the phosphorus containing polyols of the formula (II) are autocatalytic, i.e. they will catalyze the reaction between the polyisocyanate and the polyol without the need for other catalysts to be employed. However, in certain instances, for example, where a very fast reaction is desired or where the proportion of compound (II) employed in the polyurethane forming reaction is low, it may be necessary to include a conventional polyurethane catalyst in the reaction mixture. Many such catalysts are known; see, for example, Saunders et al., ibid, Part I, pages 228–232 and Britain et al., J. Applied Polymer Science, 4, pp. 207–211, 1960. Illustrative of these catalysts are organic and inorganic salts of, and organometallic derivatives of, bismuth, lead, tin, iron, antimony, uranium, cadmium, cobalt, thorium, aluminum, mercury, zinc, nickel, cerium, molybdenum, vanadium, copper, manganese, and zirconium, as well as phosphines and tertiary organic amines. Representative organotin catalysts are stannous octoate, stannous oleate, dibutyltin dioctoate, dibutyltin laurate, and the like. Representative tertiary organic amine catalysts are triethylamine, triethylenediamine, N,N,N',N'-tetramethylethylene-diamine, N,N,N',N'-tetraethylethylenediamine, N-methylmorpholine, N-ethylmorpholine, N,N',N'-tetramethylquanidine, N,N,N',N'-tetramethyl-1,3-butanediamine, N,N-dimethylethanolamine, N,N-diethylethanolamine, and the like. Preferred catalysts for use in the process of the invention are triethylamine and triethylenediamine. The amount of catalyst employed, if one is present in addition to the compound (II), is generally within the range of about 0.1 to about 2 percent by weight based on total weight of reactants.

The blowing agents which are employed in preparation of the polyurethane foams of the invention can be any of those conventionally employed in the preparation of rigid polyurethane foams. Illustrative of said blowing agents are water (which generates carbon dioxide by reaction with isocyanate) and volatile solvents such as the lower molecular weight aliphatic hydrocarbons and highly halogenated lower-aliphatic hydrocarbons, for example, trichloromonofluoromethane, dichlorodifluoromethane, chlorotrifluoromethane, 1,1-dichloro-1-fluoroethane, 1-chloro-1,1-difluoro-2,2-dichloroethane, and 1,1,1-trifluoro-2-chloro-2-fluorobutane and the like. If desired, a mixture of water and one or more of said volatile solvents can be used as blowing agent. The final foam density of the rigid polyurethane foams produced by the process of the invention is a function of the amount of blowing agent used. In general the higher the amount of blowing agent, the lower the density of the foam.

Optional additives such as dispersing agents, cell stablizers, surfactants, flame retardants, and the like which are commonly employed in the preparation of rigid polyurethane foams can be employed in preparation of the foams of this invention. Thus a finer cell structure can be obtained if water-soluble organosilicone polymers are used as surfactants. Organosilicone polymers obtained by condensing a polyalkoxypolysilane with the monoether of a polyalkylene ether polyol in the presence of an acid catalyst are representative of those surfactants which can be used for this purpose. Other surfactants such as ethylene oxide modified polypropylene ether glycols can be used, if desired, to obtain better dispersion of the components of the foam mixture.

Other additives such as dyes, pigments, soaps and metallic powders and other inert fillers can be added to the foam mixture to obtain special foam properties in accordance with practices well-known in the art.

As discussed above, the compounds of the formula (II) display, as one of their many advantages, the ability to form storage stable polyol premixes. The latter are commonly employed as one component of a multicomponent system which is supplied as such to the ultimate user. The various components of the system are not admixed until it is desired to prepare the desired polyurethane. Thus, the various components of the polyurethane forming system may be stored over prolonged periods before use. It is eminently desirable that no change in properties, particularly in regard to relative reactivity of the polyol component including catalyst and the polyisocyanate, occur during storage otherwise the reaction occurring when the components are ultimately brought together may not proceed as desired and the properties of the resulting polyurethane may not correspond to expectations.

We have found that the polyols of the formula (II) can be stored in admixture with the polyol, a catalyst if one is employed, and other conventional additives set forth above, all of which materials are conventionally employed as a single blend in the polyol premix of multicomponent systems, and the premix so obtained shows no signs of deterioration after storage over periods of many months. Thus, even after prolonged storage, the premixes in question show no significant change in reactivity rates, as measured by cream time and rise time in the case of foams, in the reaction with the polyisocyanate component to form the desired polyurethane. Further, the physical properties of polyurethanes derived by reaction of the polyisocyanate and polyol premix, after the latter have been stored for long periods, show no significant differences from those of polyurethanes prepared by interaction of the polyisocyanate and polyol premix shortly after the latter has been prepared.

These properties of the phosphorus containing polyols (II) of the invention distinguish them from the various closely related polyols hitherto known in the art. In particular the storage stability and the autocatalytic activity of the polyols (II) distinguish them from the commonly used phosphorus containing polyols of formula (I) above.

The following examples describe the manner and process of making and using the invention and set forth the best mode contemplated by the inventors of carrying out the invention but are not to be construed as limiting.

EXAMPLE 1

Dimethyl-1,4,6,9-tetraoxa-5-phospha(5-P$^V$)spiro[4,4]-nonane

To a solution of 352 ml. (4 mole) of phosphorus trichloride in 800 ml. of methylene chloride maintained at 10° C was added, with stirring, a total of 304 g. (4 mole) of propanediol-1,2. The addition was made slowly but continuously over a period of 1 hour. The resulting product was maintained at 8° to 12° C and stirred while a total of 265.2 g. (4.4 mole) of propylene oxide was added over a period of about 20 minutes. The resulting mixture was stirred and maintained at the same temperature for a further period of 15 minutes. Thereafter the excess propylene oxide was removed by reducing the pressure in the system to about 15 mm. of mercury and maintaining this pressure for approximately 15 minutes. A total of 304 g. (4 mole) of propanediol-1,2 was then added to the residue with stirring. The temperature rose to a maximum of 40° C. The mixture so obtained was then allowed to stand at room temperature (circa 20° C) overnight before being subjected to distillation under reduced pressure, finally at 50°–60° C and 0.3 mm. of mercury, to remove volatile materials. There was thus obtained 785 g. of dimethyl-1,4,6,9-tetraoxa-5-phospha(5-P$^V$) spiro[4,4]nonane in the form of an oily liquid.

EXAMPLE 2

O,O'-di(hydroxypropyl) N,N-diethylaminomethanephosphonate

A mixture of 270 g. (1 mole) of dimethyl-1,4,6,9-tetraoxa-5-phospha(5-P$^V$)spiro[4,4]nonane and 45 g. (1.5 mole) of paraformaldehyde was heated, with stirring, to 50° C and a total of 115.3 g. (1.58 mole) of diethylamine was added slowly over a period of 2.5 hr. The temperature during the addition was maintained at 55°–60° C. When the addition was complete, it was found that some formaldehyde was still present in the reaction mixture. The temperature of the mixture was raised to 75° C and a total of 25 ml. (0.24 mole) of diethylamine was added with stirring. After a period of 30 minutes, the mixture was subjected to distillation at 50° to 60° C and a pressure of 0.3 mm. to remove volatile material. The residue was found by acid-base indicator to exhibit slight acidity. Accordingly, the product was heated to 60° C and 25 ml. (0.37 mole) of propylene oxide was added. The resulting mixture was maintained at 60° C for 1 hour and again tested for acidity. Slight acidity was detected and accordingly a second treatment with propylene oxide was carried out in exactly the same manner. After the treatment was complete, excess propylene oxide was removed under reduced pressure. The resulting product exhibited no significant acidity. There was thus obtained 432.8 g. (quantitative yield) of O,O'-di(hydroxypropyl) N,N-diethylaminomethanephosphonate, wherein the hydroxy propyl groups were mixtures of the isomeric forms represented by

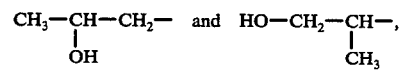

in the form of a liquid having a hydroxyl equivalent of 135 (theory 141.5).

Anal.: Calcd. for $C_{11}H_{26}O_5NP$: C, 46.64; H, 9.19; N, 4.95; P, 10.95; Found: C, 46.8; H, 9.6; N, 5.4; P, 9.3.

EXAMPLE 3

O,O'-di(hydroxypropyl) N,N-dimethylaminomethanephosphonate

A mixture of 270 g. (1.5 mole) of dimethyl-1,4,6,9-tetraoxa-5-phospha(5-p$^V$)spiro[4,4]nonane and 45 g. (1.5 mole) of paraformaldehyde was heated to 55° to 60° C with stirring and a total of 67.5 g. (1.5 mole) of dimethylamine gas was passed into the mixture with stirring over a period of 3 hours. The temperature of the reaction mixture was maintained in the range of 55° to 60° C throughout the addition. When the addition was complete, the temperature of the reaction mixture was raised to 65° C for 15 minutes and the resulting mixture was allowed to cool to room temperature (circa 20° C) and was maintained thereat overnight. Volatile materials were removed from the product by distillation under reduced pressure. The residue exhibited slight acidity by response to acid-base indicator and was therefore heated to 50° C, 30 ml. of proylene oxide was added and the mixture was agitated at about 60° C for 45 minutes before removing the excess propylene oxide under reduced pressure. The resulting product showed no significant acidity. There was thus obtained 375.6 g. (98% theoretical yeild) of O,O'-di(hydroxypropyl) N,N-dimethylaminomethanephosphonate, wherein the hydroxy propyl groups were mixtures of the isomeric forms represented by

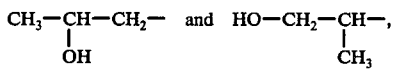

in the form of a liquid having a hydroxyl number of 104 (theory 127.5).

Anal.: Calcd. for $C_9H_{22}O_5NP$: C, 42.35; H, 8.63; N, 5.49; P, 12.16; Found: C, 42.2; H, 8.6; N, 4.7; P, 10.4.

EXAMPLE 4

Using the procedure described in Example 3, but replacing the dimethylamine there used by an equivalent amount of N-ethyl-N-methylamine, diisopropylamine, N-methyl-N-pentylamine, and dihexylamine, there were obtained the O,O'-di(hydroxypropyl)esters of N-ethyl-N-methylaminophosphonic, N,N-diisopropylaminophosphonic, N-methyl-N-pentylaminomethanephosphonic and N,N-dihexylaminomethanephosphonic acids.

EXAMPLE 5

Three polyol premixes for use in a rigid polyurethane foam forming system are prepared by intimately blending the following components in the proportions (all parts by weight) state.

| Premix | A | B | C |
|---|---|---|---|
| Amine based polyol[1] | 75 | 75 | 75 |
| Diethyl N,N-di(2-hydroxyethyl)-aminomethanephosphonate | 25 | — | — |
| Phosphorus polyol of Example 2 | — | 25 | — |
| Phosphorus polyol of Example 3 | — | — | 25 |
| Triethylamine | 1.31 | 1.31 | — |
| Water | 0.45 | 0.45 | 0.45 |
| Silicone surfactant[2] | 2.0 | 2.0 | 2.0 |
| Trichlorofluoromethane | 40.2 | 40.2 | 40.2 |

Footnotes:
[1]Polyol (eq. wt. = 131) obtained by blending (i) a polyol obtained by propoxylating a polymethylene polyphenyl polyamine containing approximately 50 percent by weight of methylenedianiline and (ii) a polyol (eq. wt. = 89) obtained by propoxylating glycerol.
[2]DC-193: Dow Corning.

It will be seen that Premix A contained a fire retardant polyol widely used commercially and Premixes B and C contained phosphorus containing polyols of the invention. Premix B contained a tertiary amine catalyst in addition to the phosphorus containing polyol, whereas Premix C did not.

Within 24 hours of their preparation, a portion of each premix was used to prepare a rigid foam by reaction with a polymethylene polyphenyl polyisocyanate having an equivalent weight of 133.5 and containing approximately 50 percent by weight of methylenebis(phenyl isocyanate). The amount of polyisocyanate employed in each case was sufficient to give a raio of NCO/OH of 1.42:1. This high ratio of NCO/OH is a feature of the particular system under test which is designed to give a low density rigid foam when poured in place in cavities in which the foam is required to rise for an extended distance in the vertical direction. It is a system in which the risk of degradation of the phosphorus containing polyol is high due to presence of water in the polyol premix.

The remainder of each of the premixes was then stored for a total of 6 months at room temperature at the end of which time the preparation of the foams was repeated using the same polyisocyanate. The data given in Table I below shows the reaction times exhibited by the three premixes before and after storage. It will be seen that the reaction times for Premixes B and C were substantially unchanged after 6 month's storage, whereas the reaction times for Premix A had increased substantially after storage for 6 months. This change (a lowering of reactivity) reflects significant deterioration of the Premix during storage.

TABLE I

| Time | Premix Reaction Times | | | | | |
|---|---|---|---|---|---|---|
| | Before Storage | | | After Storage for 6 Months | | |
| (secs.) | Premix A | B | C | Premix A | B | C |
| Mix | 10 | 10 | 10 | 10 | 10 | 10 |
| Cream | 45 | 30 | 40 | 60 | 30 | 50 |
| Gel | 195 | 90 | 140 | 330 | 80 | 160 |
| Rise | 235 | 130 | 220 | 420 | 150 | 230 |

The reaction times exhibited by Premix C illustrate the auto-catalytic activity of the polyol of the invention included therein, said activity being clearly within the practically useful range for polyurethane catalysts.

The properties of the foams derived from the above premixes after storing for less than 24 hours were as follows. The properties of the foams obtained after storage for 6 months in accordance with this particular experiment were not determined.

Foam Properties

| | Foam Premix A | B | C |
|---|---|---|---|
| Density: pcf. | 1.53 | 1.54 | 1.56 |
| Compressive strength parallel to rise; psi | 11.9 | 11.5 | 14.7 |
| % change in volume (a) after aging at 158° C and 100% humidity | | | |
| 1 day | 6.4 | 4.8 | 6.3 |
| 3 days | 8.5 | 7.2 | 9.2 |
| 7 days | 8.8 | 5.9 | 9.8 |
| 14 days | 10.6 | 6.0 | 13.0 |
| (b) after aging at 200° F and ambient humidity | | | |
| 3 days | 2.3 | 2.8 | 4.7 |
| 7 days | 4.4 | 1.6 | 3.9 |
| Oxygen index (ASTM D-2863) | 24.5 | 25.0 | 25.1 |

EXAMPLE 6

1,4,6,9-tetraoxa-5-phospha(5-$P^V$)spiro[4,4]nonane

To a solution of 44 ml. (0.5 mole) of phosphorous trichloride in 100 ml. of methylene chloride was added, slowly with stirring and cooling, a total of 31 g. (0.5 mole) of anhydrous ethylene glycol. The addition was complete in 15 minutes. The temperature of the reaction mixture throughout the addition was maintained at 6° C. The resulting product was stripped of solvent by distillation under reduced pressure and the residue was then distilled in vacuo to obtain 47.6 g. (75.3% theoretical) of 2-chloro-1,3-dioxa-pholane in the form of a fuming colorless liquid having a boiling point of 38° at 100 mm. of mercury.

A solution of 9.7 g. (0.077 mole) of the above compound in 20 ml. of methylene chloride was stirred and maintained at a temperature of about 15° C while a total of 5.8 g. (0.1 mole) of propylene oxide was added over a period of about 5 minutes. The resulting mixture was stirred and maintained at the same temperature for a short period before removing excess propylene oxide by reducing the pressure in the system to about 15 mm. of mercury. To the resulting product was added slowly, with stirring, a total of 4.8 g. (0.077 mole) of ethylene glycol. The mixture so obtained was stirred for approximately 15 minutes before removing the methylene chloride and other volatiles by distillation under reduced pressure. There was thus obtained 10.6 g. (90.6% overall yield) of 1,4,6,9-tetraoxa-5-phospha(5-P$^{IV}$)spiro[4,4-]nonane in the form of a solid.

EXAMPLE 7

Using the procedure described in Example 6, but replacing the ethylene glycol used in the second step by propylene-1,2-glycol used in the second step by propylene-1,2-glycol, there was obtained 2 (or 3)-methyl-1,4,6,9-tetraoxa-5-phospha(5-P$^{IV}$)spiro[4,4]nonane.

Similarly using the procedure described in Example 6, but replacing the ethylene glycol used in the second step by butane-1,2-diol and hexane-1,2-diol, there are obtained 2 (or 3)-ethyl and 2 (or 3)-butyl-1,4,6,9-tetraoxa-5-phospha(5-P$^{IV}$)spiro[4,4]nonane, respectively.

EXAMPLE 8

Using the procedure described in Example 1, but replacing the propylene-1,2-diol used in each step by butane-1,2-diol and hexane-1,2-diol, there are obtained diethyl- and dibutyl-1,4,6,9-tetraoxa-5-phospha(5-P$^{IV}$)spiro[4,4]nonane, respectively.

EXAMPLE 9

O,O'-di(2-hydroxyethyl) N,N-dimethylaminomethanephosphonate

Using the procedure described in Example 3, but replacing the dimethyl-1,4,6,9-tetraoxa-5-phospha(5-P$^{IV}$)spiro[4,4]nonane there used by an equimolar amount of 1,4,6,9-tetraoxa-5-phospha(5-P$^{IV}$)spiro[4,4]nonane (prepared as described in Example 6) there was obtained O,O'-di(2-dihydroxyethyl) N,N-dimethylaminomethanephosphonate in the form of a liquid. The identical material, made by a different synthetic route, was found to have the following analysis.

Calcd. for $C_7H_{16}O_5NP$: C, 37.00; H, 7.92; N, 6.16; P, 13.65; Found: C, 37.43; H, 8.21; N, 4.91; P, 13.06.

EXAMPLE 10

A rigid polyurethane was prepared using the procedure described in Example 5 but employing the following reactants and proportions (all parts by weight):

| | | |
|---|---|---|
| Amine based polyol (Ex. 5) | : | 80 |
| Di(2-hydroxyethyl) N,N-dimethylaminomethanephosphonate | : | 20 |
| Triethylamine (Ex. 9) | : | 2 |
| Organosilicone surfactant | : | 2 |
| Trichlorofluoromethane | : | 31 |
| Polymethylene polyphenyl polyisocyanate (Ex. 5) | : | 129 |

The resulting foam had excellent cell structure and appearance and was substantially free of odor. A corresponding foam made exactly as described above, but replacing the di(2-hydroxyethyl) N,N-dimethylaminomethanephosphonate by diethyl N,N-di(2-hydroxyethyl)aminomethanephosphonate, and a pronounced odor characteristic of the phosphorus polyol.

We claim:

1. An O,O'-bis(hydroxyalkyl) N,N-di(lower-alkyl)aminomethanephosphonate having the formula:

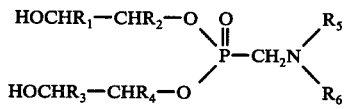

wherein $R_1$, $R_2$, $R_3$, and $R_4$ are each independently selected from the class consisting of hydrogen and lower-alkyl, and $R_5$ and $R_6$ each independently represents lower-alkyl.

2. O,O'-bis(hydroxypropyl N-N-dimethylaminomethanephosphonate.

3. O,O'-bis(hydroxypropyl) N,N-diethylamninomethanephosphonate.

4. A compound according to claim 1 wherein each of $R_1$, $R_2$, $R_3$ and $R_4$ is hydrogen and $R_5$ and $R_6$ are methyl, said compound being O,O'-di(2-hydroxyethyl) N,N-dimethylaminomethanephosphonate.

* * * * *

UNITED STATES PATENT OFFICE
CERTIFICATE OF CORRECTION

Patent No. 4,112,014    Dated September 5, 1978

Inventor(s) Curtis P. Smith and Henri Ulrich

It is certified that error appears in the above-identified patent and that said Letters Patent are hereby corrected as shown below:

Column 3, line 46:

linkage (a) or (b)

Should read:

linkage (a') or (b')

Column 3, line 58:

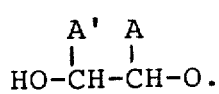

Should read:

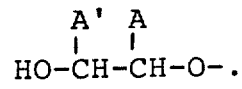

Column 3, lines 60 and 61:

group spirocyclic compound quantitative

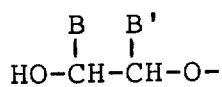

Should read:

group

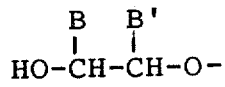

Column 10, line 51:

phospha(5-$p^V$)

Should read:

phospha(5-$P^V$)

UNITED STATES PATENT OFFICE
CERTIFICATE OF CORRECTION

Patent No. 4,112,014　　　　　　　　　　Dated September 5, 1978

Inventor(s) Curtis P. Smith and Henri Ulrich

It is certified that error appears in the above-identified patent and that said Letters Patent are hereby corrected as shown below:

| | |
|---|---|
| Column 11, line 29: | Should read: |
| are prepared | were prepared |
| Column 11, line 57: | Should read: |
| amont | amount |
| Column 11, line 58: | Should read: |
| raio | ratio |
| Column 12, line 61: | Should read: |
| 100 mm. | 10 mm. |
| Column 13, lines 16 and 17: | Should read: |
| -1,2-glycol, used in the second step by propylene-1,2-glycol, there was | -1,2-glycol, there was |

UNITED STATES PATENT OFFICE
CERTIFICATE OF CORRECTION

Patent No. 4,112,014      Dated September 5, 1978

Inventor(s) Curtis P. Smith and Henri Ulrich

It is certified that error appears in the above-identified patent and that said Letters Patent are hereby corrected as shown below:

| | |
|---|---|
| Column 13, line 43: | Should read: |
| O,O'-di(2-dihydroxyethyl) | O,O'-di(2-hydroxyethyl) |
| Column 14, line 1: | Should read: |
| $C_7H_{16}O_5NP$: | $C_7H_{18}O_5PN$: |
| Column 14, claim 3, line 40: | Should read: |
| N,N-diethylamnino | N,N-diethylamino |

Signed and Sealed this

Twenty-sixth Day of February 1980

[SEAL]

Attest:

SIDNEY A. DIAMOND

Attesting Officer

Commissioner of Patents and Trademarks